United States Patent [19]

Cohen

[11] 4,341,213

[45] Jul. 27, 1982

[54] BONDED NONWOVEN FABRICS

[75] Inventor: Lawrence B. Cohen, Sharon, Mass.

[73] Assignee: The Kendall Co., Boston, Mass.

[21] Appl. No.: 292,374

[22] Filed: Aug. 13, 1981

[51] Int. Cl.$^3$ .............................................. A41B 13/02
[52] U.S. Cl. ..................................... 128/284; 128/287;
128/290 R; 428/198; 428/206; 428/283;
428/288; 428/290; 428/323; 428/325; 428/331;
428/447; 428/454; 428/913; 428/920; 524/425;
524/426; 524/437; 524/446; 524/535; 524/560;
524/561; 524/562; 524/563; 524/575
[58] Field of Search ............... 128/284; 428/198, 283,
428/288, 290, 323, 325, 331, 359, 360, 361, 913,
920, 447, 451, 452, 454, 206; 260/29.6 CM, 29.6
R, 29.7 R

[56] References Cited

U.S. PATENT DOCUMENTS

| | | | |
|---|---|---|---|
| 3,278,365 | 10/1966 | Adams et al. | 428/454 |
| 3,380,877 | 4/1968 | Smucker et al. | 428/391 |
| 3,597,268 | 8/1971 | Smith | 428/391 |
| 3,619,281 | 11/1971 | Kroning et al. | 427/381 |
| 3,639,156 | 2/1972 | Pittman et al. | 428/254 |
| 3,650,814 | 3/1972 | Elder | 428/405 |
| 3,716,517 | 2/1973 | Pittman et al. | 528/34 |
| 3,904,805 | 9/1975 | Johnson et al. | 428/378 |
| 3,935,363 | 1/1976 | Burkholder et al. | 428/454 |
| 4,035,540 | 7/1977 | Gander | 428/198 |
| 4,218,359 | 8/1980 | Marwitz et al. | 428/446 |
| 4,263,082 | 4/1981 | Temple | 428/392 |
| 4,316,931 | 2/1982 | Tischer et al. | 428/288 |

*Primary Examiner*—James J. Bell

[57] ABSTRACT

Nonwoven fabrics are bonded by a binding agent which comprises an aqueous dispersion of an organic polymer coupled to an inorganic filler by means of an organosilane or organotitanate coupling agent. Such fabrics possess properties which render them exceptionally suitable for use as top sheets for disposable diapers and the like.

8 Claims, No Drawings

BONDED NONWOVEN FABRICS

The present invention relates to nonwoven fabrics comprising a fibrous array bonded by a bonding agent which comprises a water-dispersed polymeric binder coupled to an inorganic filler by means of a monomeric organosilane or organotitanate.

BACKGROUND OF THE INVENTION

Nonwoven fabrics, composed of unspun and unwoven fibers or filaments in which the fibers or filaments are adherently united to each other along at least certain portions of their length by means of an organic polymeric bonding agent, are a staple article of commerce. The base fabric may be an array of textile-length fibers, customarily of one to six inches in length, formed into a fleece or web by means of a card, garnett, air-lay device, or other web-forming device. Alternatively, the fabric may be composed of very short fibers, down to and including fibers of papermaking length, formed by known wet-lay or dry-lay processes, or the fabric may include textile-length fibers intermingled with papermaking fibers. Another category of nonwoven fabrics includes those formed from continuous filaments, extruded from spinerettes to form an unbonded or lightly bonded fleece. The present invention is applicable to all fibrous or filamentary arrays which are to be bonded to impart sufficient strength and integrity to the array to meet the requirements of the end use to which they are to be put.

Conventionally, the fibrous arrays are bonded by organic polymeric bonding agents in the form of aqueous dispersions or latices. Such polymeric latices are effective bonding agents, but they are often expensive compared with the cost of the fibers in the fabric, and they are for the most part flammable by nature when in the dry state as a component of a nonwoven fabric. Attempts have been made to add inorganic fillers to polymeric latices to decrease the cost of the bonding agent and to reduce the flammability, but effective loading with such fillers thickens the latex, while decreasing the tensile strength of the finished nonwoven fabric by an undesirable margin. Similarly, attempts to reduce the flammability of polymer-bonded nonwoven fabrics by treatment with flame-retardant finishes such as sulfamates, complex organophosphates, and the like, pose problems of irritation and potential toxicity.

BRIEF DESCRIPTION OF THE INVENTION

It has now been found that substantial amounts of inorganic fillers containing adsorbed water bonded to their surfaces or as part of their structure may be added to a polymeric latex with no significant thickening or viscosity increase if the inorganic filler is first reacted, in aqueous suspension, with certain monomeric organosilanes or organotitanates, as set forth more fully hereinbelow. The formation of such filled bonding agents greatly decreases the flammability of nonwoven fabrics, while not substantially decreasing the tensile strength of the fabric, and in many cases even increasing the strength.

NATURE OF THE INVENTION

The basic reaction involved in the present invention is a modification of a reaction used in the molded plastics field, and the application of this modified reaction to the bonding of nonwoven fabrics. It is known, for example, to use certain monomeric organosilanes and organotitanates to couple selected inorganic fillers to dry polymeric dispersions by milling the ingredients together, to improve certain properties in such articles as cable coverings, gaskets, floor tiles, and other molded articles.

It has now been found that certain monomeric organosilanes and organotitanates may be used to couple selected inorganic fillers to the dispersed polymer in aqueous polymeric latices, with an unexpected enhancement in the properties of nonwoven fabrics bonded with such agents.

A brief summary of a convenient process of the invention comprises as an initial step dissolving the desired amount of coupling agent in water, with the addition of a trace of an anti-foaming agent if needed. To hasten the dissolving of difficultly soluble coupling agents, they may be initially dissolved in alcohol or a glycol if necessary. The water temperature is preferably 20° C.–85° C., and the filler is then gradually added to the aqueous solution with agitation, which is continued to 0.125 to 2 hours, depending on the efficiency of agitation, to insure maximum interaction of filler and coupling agent.

If pH adjustment agents and surfactants are desired in the final binder system they are added to the aqueous suspension, followed by the calculated amount of polymeric latex to bring the system to the desired concentration. The binder is then applied to a fibrous web and dried by conventional means. Drying the fabric completes the reaction between the filler-coupler product and the polymer in the latex, and post-curing the fabric at elevated temperatures enhances the wet-strength of the product by as much as 60% over the strength of the uncured product.

Inorganic fillers suitable for use in the practice of this invention include alumina trihydrate, $Al_2O_3.3H_2O$; silica, $SiO_2$; calcium carbonate; clays such as those composed of aluminum or magnesium silicates; and other finely-divided inorganic materials which have adsorbed water bound to their surfaces, or as a structural element. The particle size of the inorganic filler should be less than 10 microns, with a preferred range of 0.5–3.0 microns. In general, the loading factor or ratio of filler to the polymer content of the latex lies between 0.2 to 3.0 parts filler to one part polymer, with a preferred range of 0.2 to 1.5 parts. The amount of coupling agent may range from 0.1 to 2.0 parts per 100 parts of filler, with a preferred range of 0.25 to 1.0 parts per 100 parts of filler.

A wide variety of polymeric latex emulsions may be employed in the process of this invention, including but not restricted to: acrylic esters, styrene-acrylic esters, and vinyl acetate-acrylic ester copolymers, as well as vinyl acetate homopolymers, all of which may include acrylic acid and crosslinking agents such as N-methylolacrylamide. Also suitable are styrene-butadiene rubber emulsions, ethylene vinylacetate copolymers, and the like.

A variety of coupling agents may be utilized in the present invention, the principal consideration being that the organosilane or organotitanate preferably contain at least one organic group, capable of hydrolyzing in aqueous media, covalently bonded to the silicon or titanium atom, and at least one non-hydrolyzable organic group covalently bonded to the silicon or titanium atom, the non-hydrolyzable group being capable of coupling with the polymeric bonding agent by means of a combination of covalent bonding and Van der Waals forces. Such coupling agents are known in the art and are commercially available.

One exception to the above generalization is the case of organotitanates wherein two titanium valences are taken up by certain chelate linkages. Such coupling agents, discussed more fully hereinbelow, are useful in the practice of this invention although they are stable to hydrolysis in aqueous media.

Typical silane coupling agents suitable for the practice of this invention may be represented by the general formulas $(RO)_mSi[(CH_2)_yY]_{4-m}$ and $(RO)_mSi(R_1)_x[(CH_2)_yY]_n$, wherein in the first case (RO) is a hydrolyzable alkoxy or acetoxy group such as $CH_3O-$, $C_2H_5O-$, $CH_3COO-$, or the like. The $(CH_2)_yY$ group is an organofunctional group in which y is preferably 0 to 4 and Y is a group selected from, for example, amino, vinyl, epoxy, hydroxy, halogen, or methacryloxy. Preferred groups include $-NH_2$, $-NHCH_2CH_2NH_2$, $-CH=CH_2$, and $-OCOC(CH_3)=CH_2$. In the second case, of the $(RO)_mSi(R_1)_x[(CH_2)_yY]_n$, $R_1$ is preferably an alkyl group of from 1 to 4 carbon atoms, (RO) and $(CH_2)_yY$ have the values as above, and $m+n+x=4$.

Representative useful silanes include $CH_2=CH-Si(OC_2H_5)_3$, $CH_2=CH-Si(OCH_2CH_2OCH_3)_3$, $CH_2=C(CH_3)-CO-O-CH_2CH_2CH_2-Si(OCH_3)_3$, $H_2NCH_2CH_2CH_2-Si(OC_2H_5)_3$, $H_2NCH_2CH_2NHCH_2CH_2CH_2-Si(OCH_3)_3$,

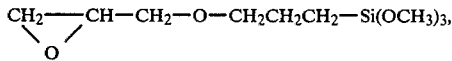

and the like.

The general course of the reaction is presumed to be hydrolysis of the (RO) groups to from-SiOH groups, followed by condensation of the polar-SiOH groups with $-OH$ groups present in the form of adsorbed water on the inorganic filler or as an element of the structure thereof, with the formation of a coupling agent-filler complex. The organophilic portion of the coupling agent then covalently bonds with the organic latex polymer.

Titanium analogs of the above organosilanes may also be used in the practice of this invention, in addition to organotitanates of the general formula $(RO)_aTi[X(CH_2)_nY]^b[X'(CH_2)_mY']_c$, wherein $a+b+c=4$; RO is a hydrolyzable alkoxy or acetoxy group; X and X' are O, $PO_3$, $HP_2O_6$, m and n are 1 to 17 with a preferred range of 2 to 8; and Y and Y' are such groups as $-H$, $-NHC_2H_4NH_2$, $-NHC_2H_4NHC_2H_4NH_2$, $-OC_2H_4OC_2H_4NH_2$, $-OCOC(CH_3)=CH_2$,

and the like. Also useful are organotitanates similar to the above formula wherein the (RO) group is replaced by a chelating ligand occupying two of the titanium valences. Suitable chelates may be formed, for example, from alpha hydroxy acids such as $RCH_2(OH)COOH$, where $R=H$ or an alkyl group, or from a glycolate, such as $HO-CH_2(R)-CH_2=OH$ wherein again $R=H$ or an alkyl group.

When Y and Y' are H in the above formulas for organotitanates, the coupling between filler and polymer is in part presumably due to Van der Waals forces.

When X and X' are $HP_2O_6$, water solubility may be facilitated by quaternization with $R_1R_2R_3N$ where $R_1$, $R_2$, and $R_3$ are H or lower alkyl groups.

Representative organotitanates suitable for use in this invention include, in addition to the titanium analogs of the silanes, such coupling agents as $(CH_3)_2CHO-Ti[OC_2H_4NHC_2H_4NH_2]_3$,

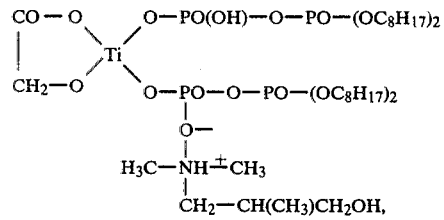

$(CH_3)_2CHO-Ti[OC_2H_4NHC_2H_4NHC_2H_4NH_2]_3$, and $(CH_3)_2CHO-Ti[OC_2H_4OC_2H_4NH_2]_3$. Other coupling agents of the Si or Ti type suitable for this use will readily suggest themselves to those skilled in the art.

PREFERRED EMBODIMENT OF THE INVENTION

To 120 lbs. of water at 40°–180° F. there is added 22 grams of a silicone antifoam agent such as Dow H-10, a product of Dow Chemical Corporation, with agitation. After brief mixing, 155 grams of a coupling agent, the dimethylamine methylpropanol salt of titanium di(dioctylpyrophosphate) oxyacetate, known as KR-138D, a product of Kenrich Petrochemical Company, are added to the water and agitation is continued for 10 minutes, after which 34.13 pounds of finely-divided $Al_2O_3\cdot 3H_2O$ are added. After 30 minutes of continued agitation, the viscosity of the suspension is less than 20 centipoises: in the absence of the coupling agent, a similar suspension has a viscosity of over 3,000 centipoises. The suspension is further diluted with 160 pounds of water, after which 124 grams of a wetting and emulsifying agent (Triton X-100, a product of Rohm and Haas) and 400 grams of an additional wetting agent (Gafac RS-410, a product of General Aniline and Film Corp.), each in 15 lbs. of hot water are added to the suspension. The final addition, with stirring is 77.57 pounds of latex, a copolymer of ethyl and butyl acrylates of 44% solids content.

The result is 424 pounds of mixture of 16.1% solids content, having a viscosity of under 25 centipoises and a surface tension of less than 37 dynes.

This latex-filler combination is then applied by conventional methods to a carded web of polyester fibers, weighing 14.7 grams per square yard, in a continuous process. Wet pickup is adjusted to 290%, adding 6 grams of binder to each square yard of fibrous web. Drying is by means of steam-heated dry cans at a temperature of 250°–375° F. (121°–191° C.)

The dried bonded product, weighing about 21 grams per square yard, is composed of 70% fiber, 15% polymer, and 15% alumina trihydrate. Despite the low polymer content, products prepared in accordance with this invention have adequate strength to serve numerous uses where wet tensile strength is a criterion.

The fabric prepared according to the above embodiment of the invention may be made quite inexpensively in comparison with fabrics which use polymeric latices as the sole binding agent. It transmits moisture readily, has a low degree of capillary spread of moisture, and resists rewetting when in contact with moist substrates. These properties make the fabric eminently suitable for use as a cover sheet for disposable diapers, drainage pads, surgical dressings, and similar uses.

ADDITIONAL EMBODIMENTS OF THE INVENTION

As an illustration of the use of a silane coupling agent, to 180 pounds of water at 140°-160° F. there is added 22 grams of Dow H-10 silicone antifoam, with adjustment of the pH to 4.0 with the addition of acetic acid. After mixing, 45 grams of a silane coupling agent, gamma-aminopropyl-trimethoxysilane, dissolved in 268 grams of propylene glycol, and 19.8 pounds of alumina trihydrate were added. Agitation was continued for 30 minutes. After which 103 pounds of water were added, followed by 108 grams of Triton X-100 dissolved in 15 pounds of hot water and 400 grams of Gafac RS-410 in 15 pounds of hot water. Finally, 90 pounds of latex, the same type as used in the preferred embodiment above, were added and agitation was continued until mixing was complete. The finished mixture had a viscosity of 4 centipoises, a surface tension of less than 37 dynes, and a solids content of 14.3%. It was applied to a carded web of polyester fibers and then dried in a procedure similar to the preferred embodiment, above, yielding a comparable product in weight and content.

It is characteristic of the products of this invention that a post-curing at elevated temperatures, after the initial drying, will in general effect a marked increase in the wet cross-directional tensile strength, or WCDT, which is usually the weakest and at the same time most important parameter in the tensile properties of carded nonwoven fabrics. In the case of the example just described, the WCDT of a 1-inch wide strip was 197 grams, rising to 254 grams after 5 minutes post-cure at 350° F., an increase of 29%. Longer post-cure exposures of up to 30 minutes, may lead to WCDT increases of over 50%. By contrast, fabrics bonded with amounts of latex equal in amount to the latex-filler complexes illustrated in the above examples, but without employing filler or coupling agent, will show an increase of less than 10% in WCDT after post-curing.

It is also characteristic of the products of this invention that inexpensive fillers may be used to enhance the strength of nonwoven fabrics in an unexpected manner.

For example, using the general procedure of the above preferred example but employing a styrene-acrylic ester copolymer latex, a paired set of fabrics was prepared, each fabric containing approximately the same amount of polymer and the same amount of alumina filler. One fabric was prepared using K-138D as a coupling agent; the coupling agent was omitted from the other fabric. The final weights of both fabrics were comparable.

|  | Coupling Agent | % Polymer in Product | % Filler in Product | Wet Cross Directional Strength, grams/inch strip |
|---|---|---|---|---|
| Example A | K-138D | 14.8% | 14.8% | 238 gm. |
| Example B | none | 16.8% | 16.8% | 138 gm. |

In spite of the fact that the fabric of Example A had less polymeric binder holding the fibers together, it had a wet tensile strength in the cross direction that was 72% greater than in the case of Example B, a duplicate of Example A except for the omission of the coupling agent.

It is apparent, therefore, that the use of coupling agents in the production of nonwoven fabrics in accordance with this invention enhances the wet strength of the product to an unexpected degree. In a third controlled experiment, similar to Examples A and B except that no alumina trihydrate and no coupling agent were used, the same polymeric latex was applied to a similar fibrous web at a level of 15.8%. The wet cross direction tensile strength was 176 grams per inch-wide strip. The use of the coupling agent, therefore, has enabled inert inorganic fillers to be introduced in a form in which the wet tensile strength is not only not decreased, as might be expected, but is actually increased by up to 35% or more.

Additionally, nonwoven fabrics thus produced, with an alumina trihydrate content of 30 or more parts per 100 parts of polymer are classed as Class I products according to NFPA Section 702. They can be ignited, but are self-extinguishing in less than five seconds, and in the case of fabrics consisting of polyester fibers, or similar synthetic fibers which tend to melt when heated, there is no drip of molten fiber substance. This is advantageous in the case where either potentially toxic or irritating flame retardants must be used, or warnings about flammability must accompany the fabric. Presumably the flame-retardant properties of the fabric are due the inherent non-flammability of $Al_2O_3$, together with the heat-sink provided by the three molecules of water of composition.

Still a further characteristic of the products of this invention is that they are marked by an unusual surface softness when compared with fabrics bonded by polymer alone. Although the viscosity, surface tension, and other obvious properties of polymer suspensions and polymer-coupling agent-filler suspensions are not significantly at variance, the suspensions show a marked difference in their distribution in a bonded nonwoven fabric. In the case of polymer-coupling agent-filler suspensions, a given amount of total complex will appear as a relatively smooth and even coating along the fibers substantially throughout the thickness of the dried fabric. In the case of an equal amount of polymeric latex alone, there is a marked concentration of polymer in the form of irregular beads or aggregates at or near the surface of the fabric, resulting in a surface stiffness or boardiness which is esthetically undesirable in such products as disposable diaper top sheets.

Diaper top sheets prepared in accordance with this invention characteristically weight from 13 to 50 grams per square yard, and consist of between 50% and 80% fiber, 50% and 20% binder comprising polymer-coupling agent-inorganic filler as described above. Typically, such top sheets should have a wet cross-directional tensile strength of at least 160 grams per inch-wide strip. As described above, such top sheets transmit moisture readily, have low capillarity, and resist rewetting when in contact with moist substrates.

What is claimed is:

1. A nonwoven fabric which comprises an unspun and unwoven array of textile fibers adhesively united to each other along at least certain portions of their length by a combination of
   (a) an organic polymeric bonding agent;

(b) an inorganic filler selected from the class consisting of alumina trihydrate, silica, calcium carbonate, and clays having adsorbed water bound to their surfaces or as an element of their structure, said organic polymeric bonding agent being coupled to said inorganic filler by (c) a coupling agent selected from the class consisting of (d) organosilanes and organotitanates characterized by having covalently bonded to the silicon or titanium atom at least one organic group capable of hydrolyzing to a hydroxy group in aqueous media, and further characterized by having at least one non-hydrolyzable organic group covalently bonded to said silicon or titanium atoms, and (e) organotitanates in which two valences of the titanium atom are taken up by a non-hydrolyzable chelate linkage.

2. The nonwoven fabric according to claim 1 wherein the fibers are of textile length, capable of being formed in an intermingled array by means of textile equipment such as cards, garnetts, and air-lay devices.

3. The nonwoven fabric according to claim 1 wherein the fibers continuous filaments.

4. The nonwoven fabric according to claim 1 wherein at least a portion of the fibers are of paper-making length.

5. The nonwoven fabric according to claim 1 wherein the inorganic filler is present to the extent of between 25% and 150% of the weight of the polymer in the polymeric latex.

6. The nonwoven fabric according to claim 1 wherein the coupling agent is present to the extent of from 0.1% to 2.0% of the weight of the inorganic filler.

7. The nonwoven fabric according to claim 1 wherein the fabric is self-extinguishing after ignition.

8. A top sheet for a disposable diaper, comprising an array of intermingled fibers bonded by a bonding agent according to claim 1, said top sheet having a weight of between 13 and 50 grams per square yard and a wet cross-directional tensile strength of at least 160 grams per square yard.

* * * * *